United States Patent [19]

Meijer et al.

[11] Patent Number: 4,818,425

[45] Date of Patent: Apr. 4, 1989

[54] PROCESS FOR THE PREPARATION OF DIPEROXYDODECANEDIOIC ACID-CONTAINING AGGLOMERATES AND COMPOSITIONS IN WHICH THESE AGGLOMERATES ARE USED AS BLEACHING COMPONENT

[75] Inventors: John Meijer, Deventer; Reinder Torenbeek, Terwolde; Rolf H. van den Berg, Kring Van Dorth, all of Netherlands

[73] Assignee: Akzo N.V., Arnhem, Netherlands

[21] Appl. No.: 51,752

[22] Filed: May 20, 1987

[30] Foreign Application Priority Data

May 28, 1986 [NL] Netherlands ........................ 8601361
Jan. 19, 1987 [NL] Netherlands ........................ 8700107

[51] Int. Cl.$^4$ ...................... C11D 3/395; C01B 15/00; C07C 179/10

[52] U.S. Cl. ........................................ 252/94; 252/95; 252/174.13; 252/186.26; 252/186.38; 23/313 R; 427/212; 427/213.3; 260/502 R; 264/117

[58] Field of Search ............ 264/117; 427/212, 213.3, 427/220; 260/502 R; 252/174.13, 186.26, 186.38, 94, 95; 23/313 R

[56] References Cited

U.S. PATENT DOCUMENTS 3,847,830 11/1974 Williams et al. .............. 252/186.26
3,925,234 12/1975 Hachmann et al. ................ 252/102
4,013,581 3/1977 Huber ........................... 252/186.26
4,091,544 5/1978 Hutchins .................................. 34/9
4,100,095 7/1978 Hutchins et al. ..................... 252/95
4,119,660 10/1978 Hutchins ......................... 260/502 R
4,128,495 12/1978 McCrudden .................. 252/186.26
4,172,086 10/1979 Berkowitz ....................... 260/502 R
4,233,235 11/1980 Camden et al. ................. 260/502 R
4,314,949 2/1982 Bettle, III et al. ............. 260/502 R
4,443,352 4/1984 Bronze et al. ......................... 252/95
4,642,198 2/1987 Humphreys et al. ................. 252/95
4,655,780 4/1987 Chun et al. .......................... 427/212

FOREIGN PATENT DOCUMENTS 0127783 5/1984 European Pat. Off. .
911410 11/1962 United Kingdom .
1387167 3/1975 United Kingdom .
1456591 11/1976 United Kingdom .

*Primary Examiner*—Paul Lieberman
*Assistant Examiner*—Helene Kirschner
*Attorney, Agent, or Firm*—Parkhurst, Oliff & Berridge

[57] ABSTRACT

A process for the preparation of agglomerates containing diperoxydodecanedioic acid and a water-impermeable material, e.g. lauric acid, which process comprises the successive steps of agitating an aqueous suspension of the peroxy acid in the presence of the water-impermeable material and above the melting point thereof, cooling the suspension of the agglomerated particles thus obtained to a temperature at which the water-impermeable material turns solid, and isolating the resulting agglomerates. The agglomerates obtained are suitable for use as bleaching agent.

6 Claims, No Drawings

PROCESS FOR THE PREPARATION OF DIPEROXYDODECANEDIOIC ACID-CONTAINING AGGLOMERATES AND COMPOSITIONS IN WHICH THESE AGGLOMERATES ARE USED AS BLEACHING COMPONENT

The invention relates to a process for preparing agglomerates containing an aliphatic diperoxydicarboxylic acid and a water-impermeable material solid at room temperature, which process comprises the successive steps of agitating an aqueous suspension of the acid in the presence of the water-impermeable material in an amount of at least 25% by weight, calculated on the acid, for at time sufficient to agglomerate the suspended acid particles and at a temperature above the melting point of the water-impermeable material and below the decomposition temperature of the acid, cooling with continued agitation of the suspension of the agglomerated particles thus obtained to a temperature at which the water-impermeable material turns solid, and isolating the resulting agglomerates. The invention also relates to shaped particles which in addition to the agglomerates thus prepared contain a hydratable material, and to compositions such as detergent and bleaching compositions in which these agglomerates are used as bleaching component. A process as indicate above is disclosed in British Patent Specification No. 1,387,167. As aliphatic diperoxydicarboxylic acids it mentions diperoxyadipic acid and diperoxyazelaic acid. It also states that the agglomerates should be coated with a water-soluble, inorganic hydrate-forming salt having a pH in a 1% by weight aqueous solution of at least 10.5 in order to eliminate or at least much reduce the incidence of pin point spotting during the use of the agglomerates as bleaching agent for dyed fabrics. To the use of such a coating, however, there are several disadvantages. In the first place, its application involves an additional step in the preparation of the bleaching agent, which makes the preparation cumbersome. In the second place, the chemical stability of the diperoxydicarboxylic acid during storage of the bleaching agent will be impaired by the closely adjacent alkaline salt. In the third place, the water-solubility of the coating makes it impossible for the bleaching agent to be taken up as bleaching component in concentrated, aqueous, pourable bleaching compositions and detergent and bleaching compositions.

The invention has for its object to meet these drawbacks. Surprisingly, it has been found that if in the process to which the invention relates the aliphatic diperoxydicarboxylic acid is 1,12-diperoxydodecanedioic acid, the resulting agglomerates may be used as such without the incidence of pin point spotting, i.e. without the need for a coating of an alkaline salt as described in the afore-mentioned British patent specification.

It should be added that U.S. Pat. No. 4,119,660 discloses surrounding peroxy acids, amongst which 1,12-diperoxydodecanedioic acid, with a coating and moreover mentions that the bleaching compositions described in said disclosure may be prepared by usual methods. As one of these methods it mentions agglomeration. There is no question, however, of an agglomeration in an aqueous suspension of the peroxy acid. In said U.S. patent specification it is further indicated that the proportion of coating material to be used should be in the range of about 2.5 to 15% by weight, calculated on the peroxy acid. As appears from experiements (see also in Examples below), such amounts of coating material do not lead to satisfactory results when 1,12-diperoxydodecanedioic acid is provided with a coating by agglomeration in an aqueous suspension of this acid.

That the agglomeration of diperoxy acids in an aqueous suspension of these acids is of importance will be apparent from the generally known great hazards (explosion) involved in working with diperoxy acids in the solid or high-concentrated state. The present process therefore provides a simple and especially safe way of making 1,12-diperoxydodecanedioic acid accessible for various uses in actual practice.

It should be added that British Patent Specification No. 1,456,591 discloses the preparation of granular bleaching compositions containing 1–40% by weight of an organic peracid, 1.5–45% by weight of a mixture of magnesium sulphate and an alkali metal sulphate and 5–45% by weight of water of hydration and indicates that the granules prepared may be coated with an encapsulating material such as fatty acids, fatty alcohols, fatty esters and polyvinyl alcohol in an amount of 1–80% by weight, calculated on the total composition. Moreover, as one of the methods used it mentions agglomeration. The present method, however, is not disclosed in said specification, nor can it be derived therefrom. This is all the more evident in that the presence of inorganic salts in the granules described in said disclosure excludes the employment of agglomeration in an aqueous suspension of the peracid.

It should also be noted that British Patent Specification No. 911,410 discloses the preparation of granular bleaching compositions coated with a fatty acid containing 10–22 carbon atoms, such as lauric acid. The only bleaching agents mentioned, however, are N-chloro compounds; nor is it known from said publication that the encapsulation may be provided by agglomeration, let alone agglomeration in suspension.

Hereinafter DPDA will be used as an abbreviation for 1,12-diperoxydodecanedioic acid.

The amount of DPDA that should be present in the suspension is generally in the range of 2 to 20% by weight, preferably 5 to 20% by weight and more particularly 10 to 18% by weight, calculated on the weight of the total suspension.

The greatest dimension of the suspended DPDA particles should be in the range of 0.5 to 100 microns and preferably 0.5 to 50 microns.

Water-impermeable materials which are suitable for use in the process according to the invention should have a melting point in the range of 30° to 80° C., and preferably 40° to 60° C. Generally, they are selected from the classes of the fatty acids, fatty alcohols and fatty esters. Preferred fatty acids are those containing 10 to 20 carbon atoms, such as stearic acid. The most preferred of this group are fatty acids having 12 to 14 carbon atoms. Particularly suitable are lauric acid and myristic acid. As fatty alcohols may be used particularly compounds containing 14 to 20 carbon atoms. As examples may be mentioned 1-tetradecanol, 1-hexadecanol and 1-octadecanol. Also mixtures of acids and mixtures of alcohols may be used. Suitable fatty acid esters are esters derived from monoalcohols as well as esters derived from polyols, such as tallow fat.

Of said water-impermeable materials the fatty acids and mixtures thereof are preferred because they will also dissolve below their melting point in an alkaline washing medium. The agglomerates prepared by means of fatty acids can therefore be used in a wide range of detergent and bleaching compositions.

It will be clear to the man skilled in the art that in the present process the water-impermeable material in the molten state will act as binder liquid. As indicated before, it should be used in an amount of at least 25% by weight, calculated on the DPDA. When use is made of less than 25% by weight, the agglomerates are difficult to isolate from the agglomeration medium and, moreover, the agglomerates will display insufficient storage stability. Further, it is recommended that the water-impermeable material should be used in an amount not higher than 100% by weight, calculated on the DPDA, as otherwise an unduly high content of inert material is obtained in the agglomerates, which would impair their use as bleaching agent. It is preferred that the water-impermeable material should be applied in an amount in the range of 28 to 66% by weight, calculated on the DPDA.

The choice of the temperature at which the agglomeration is conducted is not only dependent on the melting point of the water-impermeable material, but is also governed by other factors, such as the desired viscosity of the binder, which is of influence on the duration of the agglomeration and on the size and the strength of the agglomerates to be prepared. In any case the temperature should be chosen below 90° C., because above said temperature the DPDA is subject to unduly fast decomposition. A suitable temperature is generally one which is only a few degrees above the melting point of the water-impermeable material.

A particularly favorable embodiment of the process according to the invention consists in that the agglomeration is carried out in a suspension of the DPDA obtained after preparation of the DPDA in the usual manner by reaction of 1,12-dodecanedioic acid with hydrogen peroxide under the influence of sulphuric acid in an aqueous medium. Such usual preparation methods are described, among other places, in U.S. Pat. Nos. 4,199,660 and 4,314,949. Use of this embodiment of the invention will lead to the following important advantages. Firstly, it offers a solution to the difficulties often met in actual practice in the filtration of DPDA . Secondly, the product obtained has been desensitized in situ, so that the risks involved in working with DPDA are reduced considerably. Thirdly, from the point of view of process technique it is of advantage for the preparation and the agglomeration of DPDA to be coupled in one process.

It should be added that in situ desensitization of DPDA is also known from EP No. 127,783. In the process described in this publication the sulphuric acid contained in the resulting reaction mixture is reacted with sodium hydroxide to form sodium sulphate. Considering the relatively large amounts of neutralization heat to be carried off in that case, this method is too cumbersome for use in actual practice.

In carrying out the in situ desensitization according to the present invention it has been found that the amount of sulphuric acid present in the reaction mixture is an important parameter. Unduly high proportions thereof, such as amounts of 60–80% by weight, calculated on the total amount of sulphuric acid and water, generally lead to high-viscous suspensions which can hardly be stirred if at all after the binder has been added and the temperature has been brought to the desired value. In such cases, however, the optimum agglomeration conditions can be controlled in a simple manner by dilution with water. For instance, a sulphuric acid content not higher than 50% by weight, calculated on the total amount of sulphuric acid and water, has been found very suitable if as water-impermeable material fatty acids are employed: fatty alcohols as water-impermeable material lead to satisfactory results if the sulphuric acid content is not higher than 40% by weight, calculated on sulphuric acid and water. Moreover, the dilution heat released upon the addition of water may with advantage be used to bring the temperature of the suspension to the desired value.

In the in situ desensitization according to the present invention it has also been found that it may occasionally be of advantage for the isolated agglomerates to be heated for a short time in warm water to above the melting point of the water-impermeable material in order to remove the sulphuric acid occluded in the agglomerates. After cooling to below said melting point the agglomerates are isolated again.

The process according to the invention may be carried out by means of the equipment and stirring and isolating techniques, such as filtration and centrifuging, usually employed in such processes.

The size of the agglomerates prepared may be varied by a suitable choice of the process variables. Partly in view of the effectiveness of the agglomerates as bleaching agent it is recommended that the maximum dimension thereof should be in the range of 5 to 3000 microns, preferably 5 to 2000 microns and more particularly 5 to 1000 microns.

After the agglomerates have been isolated, they may optionally be dried in the usual manner.

In a further embodiment of the invention the agglomerates obtained are processed into shaped particles with the aid of a hydratable material. A preferred hydratable material is an inorganic salt which is non-alkaline in an aqueous solution. Examples thereof are $NaH_2PO_4$ and $KA1(SO_4)_2$. Particularly preferred is sodium sulphate.

A considerable advantage to such shaped particles is that per unit weight they contain a lower proportion of active oxygen than the agglomerates themselves, so that their use results in safer transport conditions.

The shape of the particles is preferably so chosen that they will be suitable for use as bleaching component in a solid, particulate detergent and bleaching composition. Examples of shapes suitable for this purpose are rods, flakes and granules. The greatest dimension of the shaped particles is generally in the range of 50 to 4000 microns, and preferably 50 to 2000 microns.

The shaped particles may be prepared in a manner analogous to that described for DPDA as such in U.S. No. 4,091,544. The procedure is as follows:

(a) from the agglomerates, a hydratable material, optional additives and water a pasty composition is prepared at a temperature above the hydration temperature of the hydratable material, (b) the composition obtained under(a) is broken up into particles of the desired shape, and before or after said step or during an intermediate shaping phase the material is cooled to or below said hydration temperature, and (c) the particles obtained under(b) are dried.

In Example 6 below such a preparation is described in more detail. A variant of it is described in Example 7.

The amount of hydratable material in the shaped particles is generally so chosen that per unit weight of agglomerates there are present 1 to 10 parts by weight of hydratable material, based on the weight of the material in its anhydrous form.

As examples of suitable additives that may be incorporated in the shaped particles may be mentioned sequestering agents and surface active agents. Notably, the incorporation of surface active agents is of advantage in that it has a favourable effect on the speed at which the shaped particles disintegrate in the wash liquor. It is preferred that use should be made of anionic surfactants, such as alkyl benzene sulphonates having a linear alkyl group, for instance sodium dodecyl benzene sulphonate. Other examples of additives are polymers enhancing the consistency of the shaped particles. It has been found that polyacrylic acid is very suitable for this purpose. For the greatest possible effectiveness of such additives it is recommended that they should be mixed with the agglomerates and the hydratable material in the presence of water already at the beginning of the preparation of the shaped articles.

The agglomerates prepared by the process according to the invention and the present shaped particles may with advantage be used as bleaching component in a solid, particulate fabric laundering detergent and bleaching composition. Such compositions generally contain 1 to 40% by weight of the bleaching component and 60 to 99% by weight of components commonly employed for such compositions, such as anionic, nonionic and amphoteric surfactants, builders, sequestering agents, dirt suspending agents, fluorescent and optical brighteners, perfumes and fillers. As typical examples of usual surfactants may be mentioned alkyl benzene sulphonates, aliphatic sulphonates, fatty alcohol sulphates, sulphates of alkoxylated fatty alcohols, addition products of ethylene oxide to fatty alcohols, ethylene oxide/propylene oxide copolymers and betaines containing a carboxyl group, a sulphate group or a sulphonate group.

The agglomerates obtained also may with advantage form part of aqueous, pourable bleaching compositions and detergent and bleaching compositions for cleaning fabrics. In such compositions the agglomerates are, of course, in the suspended state. The proportion of agglomerates in such compositions is generally so chosen that the compositions contain active oxygen in an amount in the range of 0.1 to 4% by weight, and preferably 0,1 to 3% by weight. Such compositions may contain, in addition to the agglomerates, usual surface active components such anionic and nonionic surfactants; as examples thereof may be mentioned (linear) alkyl benzene sulphonates, preferably those having 11 to 14 carbon atoms in the alkyl group, fatty alcohol sulphates, sulphates of alkoxylated fatty alcohols, alpha-olefin sulphonates, alkoxylated fatty alcohols, alkoxylated alkyl phenols and ethylene oxide-propylene oxide copolymers. Preferance is given to linear alkyl benzene sulphonates and ethoxylated fatty alcohols. The proportion of surfactant to be used may be varied with the desired pourability. The pourable compositions generally contain 0 to 20% by weight of anionic and 0 to 30% by weight of nonionic surfactant.

The pourable compositions may optionally contain one or more additives usually employed for such compositions, such as dirt suspending agents, sequestering agents, agents preventing the deposition of calcium carbonate, fluorescent and optical brightening or whitening agents, perfumes and enzymes.

To ensure satisfactory storage stability of the pourable compositions it is recommended that the pH be in the range of 1 to 5, preferably 1.5 to 4.5. The term pourable composition as used in the present specification refers to a composition which has a viscosity in the range of 1 to 1500 mPa.s, measured with a Brookfield rotational viscometer (RV type) at 20 rpm and at a temperature of 20° C.

It should be added that apart from their being suitable for bleaching or washing and bleaching purposes said pourable compositions are suitable to be used as disinfectants. As is well known, DPDA is a satisfactory biocide and when use is made of these pourable compositions, their effect is ensured also in places which are difficult of access, such as the inside of conduits.

The invention will be further described in the following examples.

EXAMPLE 1

The influence of the amount of binder on the agglomeration process was determined as follows.

In a glass reaction vessel 500 g of wet DPDA filter cake containing 4.8% of active oxygen were stirred in 1 litre of water. The greatest dimension of the DPDA particles was in the range of 0.5 to 40 microns. After the suspension had been heated to 50° C., lauric acid was added to it with vigorous stirring (use being made of a turbine mixer, stirring speed 500 rpm). Resulting agglomeration was terminated after 60 minutes by cooling to 20° C. Agglomerates were subsequently isolated from 750 g of the slurry (Type G-1 Schott glass filter, 125 mm in diameter, subatmospheric pressure 0.05 bar) and the time was measured which it took for the cake which had formed on the filter to show cracks (filtration time).

The amounts of lauric acid used and the filtration times measured are given in Table 1. This table also mentions the filtration time measured after using the water-impermeable material in the amount of 15% by weight recommended in U.S. Pat. No. 4,119,600. The results distinctly show that the process according to the invention leads to shorter filtration times than when use is made in such a process of the amount recommended in U.S. Pat. No. 4,119,660.

TABLE 1

| Wt. % lauric acid calculated on DPDA | Filtration time (sec) |
|---|---|
| 15[1] | 200 |
| 25 | 60 |
| 35 | 45 |

[1]Comparative experiment

EXAMPLE 2 (in situ desensitizing)

The procedure described in Example 1 for determining the effect of the amount of lauric acid on the agglomeration process was repeated, except that use was made of a suspension of DPDA which had been obtained as follows. In a glass reactor 272 g of an aqueous 70% by weight $H_2O_2$-solution and 1948 g of an aqueous 85% by weight $H_2SO_4$-solution were intermixed with stirring. The mixture was cooled to 30° C. Subsequently, 460 g of dodecanedioic acid were added over a period of 30 minutes, after which the reaction was continued for 120 minutes. During the reaction the temperature was kept at 30° C. by cooling. The reaction mixture obtained was diluted with water until the $H_2SO_4$ content was 35% by weight, calculated on $H_2SO_4$+-$H_2O$, after which the suspension, in which the greatest dimension of the DPDA particles was in the range of 0.5 to 50 microns, was heated to 50° C. Subsequently, the particles were agglomerated and the filtration time was measured as described in Example 1.

The filtration times measured for 15% by weight (comparative experiment), 25% by weight and 35% by weight of lauric acid were the same as those mentioned in Table 1.

After the products prepared using 15% by weight and 25% by weight of lauric acid, respectively, had been dried for 24 hours at 35° C., the storage stability was determined by measuring the loss of active oxygen (O). The results are given in Table 2.

TABLE 2

| Wt. % lauric acid, calculated on DPDA | Active 0 at start | Relative loss of active oxygen 0 (%) after 14 days at 40° C. | after 14 days at 30° C., rel. hum. 80% |
|---|---|---|---|
| 15[1] | 10.03 | 4.5 | 3.8 |
| 25 | 9,12 | 3,4 | 2,1 |

[1]Comparative experiment

This example clearly shows that applied as in situ desensitization, the process of the present invention leads to short filtration times and products displaying satisfactory storage stability and that the use of 15% by weight of lauric acid leads to poor results.

EXAMPLE 3

The procedure described in Example 1 of preparing DPDA agglomerates was repeated with the use of the amounts of lauric acid given in Table 3 below. After the isolated agglomerates had been dried for 24 hours at 35° C., their storage stability was determined by measuring the loss of active oxygen. The results are listed in Table 3. Moreover, the size of the agglomerates obtained was determined with photomicrographs. In the right hand column of Table 3 are mentioned the greatest dimensins of the smallest and of the largest agglomerates.

TABLE 3

| wt. % lauric acid, based on DPDA | Active 0 at start (%) | Relative active 0 loss (%) 14 days 40° C. | 56 days 30° C. | 56 days 20° C. | Dimensions (microns) |
|---|---|---|---|---|---|
| 15[1] | 10.03 | 4.5 | — | — | — |
| 35 | 8.36 | 3.5 | 3.3 | 2.2 | 40–250 |
| 47 | 7.71 | 2.4 | 3.1 | 2.1 | 40–500 |
| 56 | 7.17 | 2.2 | 3.1 | 1.5 | 60–500 |
| 69 | 6.68 | 2.2 | 2.5 | 1.6 | 125–500 |
| 82 | 6.21 | 2.2 | 2.3 | 1.9 | 1000–3000 |

[1]Comparative experiment

EXAMPLE 4

The in situ desensitization procedure described in Example 2 was repeated, except that as water-impermeable material (binder) myristic acid was used. To this end the DPDA suspension diluted to 40% by weight of $H_2SO_4$, calculated on $H_2SO_4+H_2O$, was heated to 55° C., after which myristic acid was added in an amount of 35% by weight, calculated on the DPDA. After 60 minutes' stirring (turbine mixer, 500 rpm) the mixture was cooled to 20° C. and 750 g of the slurry were filtered. The filtration time was about 40 seconds. The agglomerates obtained after washing and drying had an active oxygen content of 8.31. After 14 days' storage at 40° C. the relative loss of active oxygen was 2.0; after storage for 51 days at 20° C. and 30° C. the relative losses were 1.4 and 2,2%, respectively.

EXAMPLE 5

In situ desensitization were carried out as described in Example 2, except that the water-impermeable material consisted of mixtures of alcohols having average chain lengths of 14 and 16 C atoms, respectively, viz. Alfol® 14 and Alfol® 16 (both are commercial products of Condea Chemie, Germany). For these agglomerations use was made of DPDA reaction mixtures which had been diluted with water to a $H_2SO_4$ content of 20% by weight, calculated on $H_2SO_4+H_2O$.

The agglomeration with Alfol® 14 was conducted at 40° C., use being made of an amount of 42% by weight, calculated on the DPDA. A filtration time of 40 seconds was measured for 750 g of the resulting slurry. The agglomeration with Alfol® 16 was conducted at 50° C., also use being made of an amount of 42% by weight calculated on the DPDA. Also in this case a filtration time of 40 seconds was measured for 750 g of the resulting slurry.

EXAMPLE 6

Of the agglomerates described in Examples 2 and 4 containing, respectively, 35% by weight of lauric acid and 35% by weight of myristic acid as water-impermeable material shaped particles were prepared as follows.

At 40° C. 100 g of the agglomerates were mixed with 440 g of anhydrous sodium sulphate. Subsequently, water was added in an amount such that a pasty mass was formed. This mass was formed into a thin layer with the aid of a flaker, after which it was cooled to below 32.4° C., at which temperature the mass solidified due to the absorption of crystallization water by the sodium sulphate. The resulting mass was broken up into flakes having a greatest diameter of about 2 mm, which flakes were finally dried for 24 hours at 40° C. until they still contained 0.4% by weight of water.

The resulting flakes based on the agglomerates with lauric acid had an active oxygen content of 1.52%. After 14 days' storage at 40° C. the relative loss of active oxygen was 4.6%; after 56 days' storage at 30° C. the relative loss was 7.8%. The flakes obtained, which were based on agglomerates with myristic acid, had an active oxygen content of 1.55%. After 14 days' storage at 40° C. the relative loss of active oxygen was 4.5% and after 56 days' storage at 30° C. it was 4.6%.

For comparison, the above-described procedure of preparing flakes was repeated while use was made of DPDA as such (i.e. in accordance with U.S. Pat. No. 4,091,544. The flakes obtained were dried until they still contained 0,4% by weight of water; their active oxygen content was 1.51%. After 14 days' storage at 40° C. the relative loss of active oxygen was already as high as 14.9%; after 56 day's storage at 30° C. the relative loss was 18.2%.

EXAMPLE 7

Of the agglomerates described in Example 2 containing 25% by weight of lauric acid and having a predominant particle size between about 10 and about 100 microns, shaped particles were prepared as follows.

1255 g of a pulverulent filter cake containing 330 g of water and 925 g of the agglomerates were charged into an Eirich mixer together with 1700 g of anhydrous sodium sulphate, care being taken that the temperature of the materials was kept above 32.4° C. Subsequently, mixing was started and granules started to form. After the granules had acquired the desired size, the mixing operation was discontinued. The granules were removed from the mixer and allowed to cool to below 32.4° C. Finally, all the water of hydration was removed by drying in a fluid bed unit.

Sieve analysis of the practically spherically shaped granules yielded the following particle size distribution:

| size (microns) | % | size (microns) | % |
|---|---|---|---|
| <53 | 0.01 | 250-500 | 19.93 |
| 53-90 | 0.18 | 500-1000 | 61.71 |
| 90-150 | 1.97 | 1000-2000 | 4.37 |
| 150-250 | 9.89 | >2000 | 1.94 |

EXAMPLE 8 (pin point spotting test)

To establish the behaviour of agglomerates prepared by the process according to the invention with regard to pin point spotting, tests were carried out on two standard test fabrics, viz. an Immidial Black test fabric from EMPA (Switzerland) and Sunak test fabric from TNO (The Netherlands). In the tests use was made of a standard detergent of the following composition:

8% sodium linear alkyl (average $C_{11\frac{1}{2}}$) benzene sulphonate
2.9% ethoxylated (14 EO) tallow alcohol
3.5% sodium soap (13-26% $C_{12}$-$C_{16}$; 74-78% $C_{18}$-$C_{22}$)
43.7% sodium triphosphate
7.5% sodium silicate ($SiO_2$: $Na_2O$=3,3:1)
1.9% magnesium silicate
1.2% carboxymethyl cellulose
0.3% sodium ethylene diamine tetra-acetate
0.3% optical brightener (stilbene type)
21% sodium sulphate
9.7% water The tests were conducted as follows, use being made of agglomerates containing 35% by weight of lauric acid, calculated on the DPDA (DPDA/LA), and prepared in a manner analogous to that described in Example 1.

A circular-cut piece of test fabric 9.4 cm in diameter was placed on the bottom of a beaker having an internal diameter of 9.5 cm. Subsequently, 300 ml of wash liquor containing 1.8 g of the standard detergent were poured into the beaker and after the foam had disappeared, 25 mg of the agglomerates were evenly scattered over the surface of the liquid. After the agglomerates had reached the test fabric, it was left for 4 minutes. Next, the test fabric was transferred to a stop bath consisting of an aqueous solution of acetic acid (1%) and sodium bisulphite, after which it was dried and visually examined for pin point spotting (white spots on the test fabric).

The results are listed in Table 4. It also gives the results of comparative experiments carried out with agglomerates consisting of 35% by weight of lauric acid and 65% by weight of diperoxyazelaic acid (DPAA/LA), which had been prepared in a manner analogous to that used for the DPDA/LA agglomerates. Also given in the Table are the particle size distributions of the used agglomerates measured by the wet sieving method in accordance with DIN 53580. The data clearly show that whereas the agglomerates of diperoxyazelaic acid (DPAA/LA) exhibit pin point spotting, which is entirely in accordance with the teaching of British Patent Specification No. 1,387,167, the agglomerates of DPDA used under similar conditions do not display this phenomenon at all.

TABLE 4

| Agglomerates | DPDA/LA | DPAA/LA[1] |
|---|---|---|
| Particle size distribution: | | |
| <45 microns (%) | 99 | 82 |
| <100 microns (%) | 100 | 98 |
| <200 microns (%) | | 100 |
| Number of white spots on: | | |
| Sunak test fabric | 0 | >300 |
| Immidial Black test fabric | 0 | >50 |

[1]For comparison

EXAMPLE 9

In this Example the results are described of bleaching experiments carried out with the agglomerates described in Example 3 which contain 35% by weight of lauric acid, calculated on the DPDA. Also described are the results of comparative experiments carried out with pure DPDA from the same DPDA batch used as starting material for the experiments described in Example 3. The experiments (Lini test) were deliberately conducted under relatively unfavourable conditions as far as time (10 min) and temperature (30° C.) were concerned in order to be able to establish whether the presence of water-impermeable material (lauric acid) in the agglomerates has any negative effect on their bleaching action.

As test material were used cotton swatches (5 cm ×5 cm) stained with tea and red wine. The wash liquor had been prepared using tap water (concentration of calcium ions and magnesium ions: 1 mmole/1) and per liter it contained 7.5 g of the standard detergent described in Example 8. Each test mixture contained 300 ml of wash liquor, 4 g of cotton swatches, 10 iron balls and a bleaching agent as indicated in Table 5 below. In the preparation of the test mixtures the bleaching agent was added as the last component.

After bleaching (10 min., 30° C., see above) the cotton swatches were washed with tap water and dried to the air. Subsequently, the effectiveness of the bleaching agent was determined by reflection measurements carried out with a CR-110 Chromameter of Minolta. The reflections were measured of the original swatches ($R_o$), the stained swatches ($R_s$) and the bleached swatches ($R_b$), after which the stain removal (SR) was determined with the formula:

$$SR=100\,(R_b-R_s)/(R_o-R_s)$$

The results are given in Table 5. In this Table are also mentioned the pHs of the test mixtures before (initial pH) and after (end pH) bleaching. In the case of the test mixtures with an initial pH of 8,7 an appropriate amount of 1N HCl had been added to the wash liquor.

From the SR data (standard deviation: 2%) it is clear that the agglomeration of DPDA by the process of the invention has no disadvantageous effect on the bleaching action.

TABLE 5

| Test run | 1 | 2 | 3 | 4 | 5 | 6 | 7 | 8 |
|---|---|---|---|---|---|---|---|---|
| Active | 10 | 10 | 10 | 10 | 40 | 40 | 40 | 40 |

TABLE 5-continued

| Test run | 1 | 2 | 3 | 4 | 5 | 6 | 7 | 8 |
|---|---|---|---|---|---|---|---|---|
| oxygen (ppm) | | | | | | | | |
| Agglomerates | X | O | X | O | X | O | X | O |
| Pure DPDA[1] | O | X | O | X | O | X | O | X |
| Initial pH | 9.7 | 9.7 | 8.7 | 8.7 | 9.7 | 9.7 | 8.7 | 8.7 |
| End pH | 9.1 | 9.1 | 8.4 | 8.4 | 8.6 | 8.7 | 8.1 | 8.1 |
| SR (%): | | | | | | | | |
| red wine | 35.2 | 36.9 | 45.2 | 43.7 | 57.9 | 56.6 | 60.4 | 60.9 |
| tea | 20.0 | 21.1 | 22.5 | 22.6 | 43.4 | 39.4 | 37.7 | 39.2 |

[1]For comparison

We claim:

1. A process for preparing agglomerates containing an aliphatic diperoxydicarboxylic acid and a water-impermeable material solid at room temperature, which process comprises the successive steps of agitating an aqueous suspension of the acid in the presence of the water-impermeable material in an amount of at least 25% by weight, calculated on the acid, for a time sufficient to agglomerate the suspended acid particles and at a temperature above the melting point of the water-impermeable material and below the decomposition temperature of the acid, cooling with continued agitation of the suspension of the agglomerated particles thus obtained to a temperature at which the water-impermeable material turns solid, and isolating the resulting agglomerates, characterized in that the diperoxydicarboxylic acid is 1,12-diperoxydodecanedioic acid.

2. A process according to claim 1, characterized in that the amount of water-impermeable material contained in the suspension is at most 100% by weight, calculated on the 1,12-diperoxydodecanedioic acid.

3. A process according to claim 1, characterized in that the water-impermeable material is selected from the group of fatty acids having 10–20 carbon atoms, fatty alcohols having 14–20 carbon atoms, and fatty acid esters.

4. A process according to claim 3, characterized in that use is made of a fatty acid selected from the group of lauric acid, myristic acid and a mixture thereof.

5. A process according to claim 1, characterized in that as aqueous suspension of the 1,12-diperoxydodecanedioic acid there is used a suspension obtained by reacting in a manner known per se 1,12-dodecanedioic acid with hydrogen peroxide to form 1,12-diperoxydodecanedioic acid under the influence of sulphuric acid in an aqueous medium, and, if necessary, diluting the resulting reaction mixture with water.

6. A process according to claim 5, characterized in that the water-impermeable material is a fatty acid containing 10–20 carbon atoms and the sulphuric acid content is not more than 50% by weight, calculated on the total amount of sulphuric acid and water.

* * * * *

UNITED STATES PATENT AND TRADEMARK OFFICE

CERTIFICATE OF CORRECTION

PATENT NO. : 4,818,425

DATED : April 4, 1989

INVENTOR(S) : John MEIJER et al

It is certified that error appears in the above-identified patent and that said Letters Patent is hereby corrected as shown below:

Column 1, line 16, change "at" to --a--.

Column 2, line 1, change "experiements" to --experiments--.

Column 4, line 59, change "under(a)" to --under (a)--;
line 64, change "under(b)" to --under (b)--.

Column 5, line 47, change "0,1" to --0.1--.

Column 6, line 23, change "4.8%" to --4.84%--;
line 24, change "litre" to --liter--;
line 32, change "pressure" to --pressure:--.

Column 7, in TABLE 2, column 25, change "9,12" to --9.12--; change "3,4" to --3.4--; change "2,1" to --2.1--;
line 40, change "dimensins" to --dimensions--;
line 67, change "8.31." to --8.31%.--.

Column 8, line 2, change "2,2%," to --2.2%,--;
line 53, change "0,4%" to --0.4%--;
line 56, change "day's" to --days--.

UNITED STATES PATENT AND TRADEMARK OFFICE
CERTIFICATE OF CORRECTION

PATENT NO. : 4,818,425

DATED : April 4, 1989

INVENTOR(S) : John MEIJER et al

It is certified that error appears in the above-identified patent and that said Letters Patent is hereby corrected as shown below:

Column 9, line 33, change "3,3:1)" to --3.3:1)--.

Column 10, line 59, change "8,7" to --8.7--.

Signed and Sealed this

Twenty-sixth Day of December, 1989

*Attest:*

JEFFREY M. SAMUELS

*Attesting Officer* *Acting Commissioner of Patents and Trademarks*